United States Patent [19]

Yeh et al.

[11] Patent Number: 5,714,363
[45] Date of Patent: Feb. 3, 1998

[54] DEACETOXYCEPHALOSPORIN C HYDROXYLASE

[75] Inventors: Wu-Kuang Yeh; Joe E. Dotzlaf, both of Greenwood, Ind.

[73] Assignee: Eli Lilly and Company, Indianapolis, Ind.

[21] Appl. No.: 872,553

[22] Filed: Apr. 23, 1992

Related U.S. Application Data

[63] Continuation of Ser. No. 412,761, Sep. 26, 1989, abandoned.

[51] Int. Cl.$^6$ .................................................. C12N 9/02
[52] U.S. Cl. .................................................. 435/189
[58] Field of Search .................................................. 435/189

[56] References Cited

U.S. PATENT DOCUMENTS

| | | | |
|---|---|---|---|
| 1,252,973 | 1/1918 | Weber et al. | 435/188 |
| 2,689,203 | 9/1954 | Lolli et al. | 435/188 |
| 3,242,056 | 3/1966 | Dubois-Prevost | 435/188 |
| 3,637,462 | 1/1972 | Hill et al. | 435/188 |
| 3,761,420 | 9/1973 | Bogardus et al. | 435/188 |
| 4,536,476 | 8/1985 | Wolfe et al. | 435/814 |
| 4,693,977 | 9/1987 | Wolfe et al. | 435/815 |

OTHER PUBLICATIONS

Baldwin et al., "Purification and Initial Characterization of an Enzyme with Deacrtoxycephalosporin C Synthetase and Hydroxylan Activities", *Biochem J.* 245:831–841 1987.

Dotzlaf et al., "Copurification and Characterization of Deacrtoxycephalosporin C Synthetase of Hydroxylase from *Cephalosporin acremonium*", *J. Bacteriology* 169 (4):1611–1618, 1987.

Jansen et al., "Deacetoxycephalosporin C . . . *Streptomyces clavuligerus*", *J. Anitbodies*, vol. 38, No. 2, pp. 263–265, 1985.

Scheidegger et al., "Partial Purification . . . *Cephalosporium acremonium*", *J. Antibiotics*, vol. 37, No. 5, pp. 522–531, 1984.

*Primary Examiner*—Marian C. Knode
*Attorney, Agent, or Firm*—Paul R. Cantrell

[57] ABSTRACT

Deacetoxycephalosporin C hydroxylase is obtained in purified form from crude cell-free extracts via chromatography over a weak anionic exchange resin, ammonium sulfate fractionation, gel filtration, hydroxylapatite chromatography, and FPLC. The enzyme is obtained in >90% purity by further gel filtration and a second FPLC. The 28-residue amino-terminal sequence of hydroxylase is provided as well as a 9-residue amino-terminal sequence of an internal sequence and a 3-residue carboxy-terminal sequence. In addition to the efficient conversion of DAOC to DAC, the hydroxylase provided herein converts 7β-(α-aminoadipamido)-3-exomethylenecepham-4-carboxylic acid to DAC.

6 Claims, 4 Drawing Sheets

Molecular Weight of DAOC Hydroxylase

Gel Filtration

SDS-PAGE

Stoichiometric Analysis of DAOC Hydroxylase Conversion to DAC

Purification of DAOC Hydroxylase

Figure 4
Figure 4A
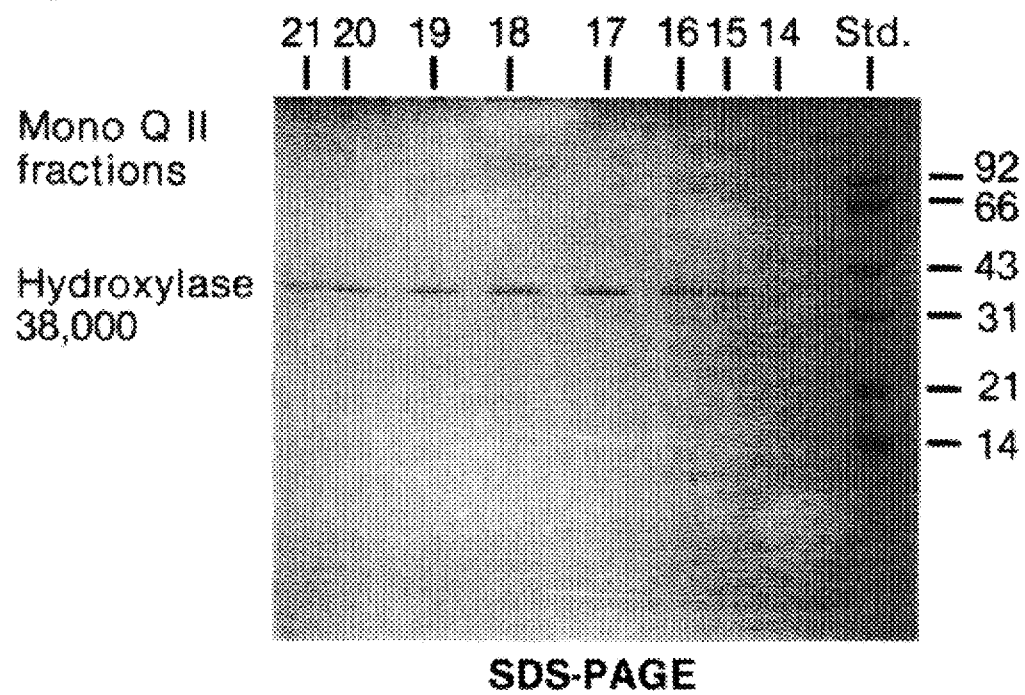
SDS-PAGE
Figure 4B
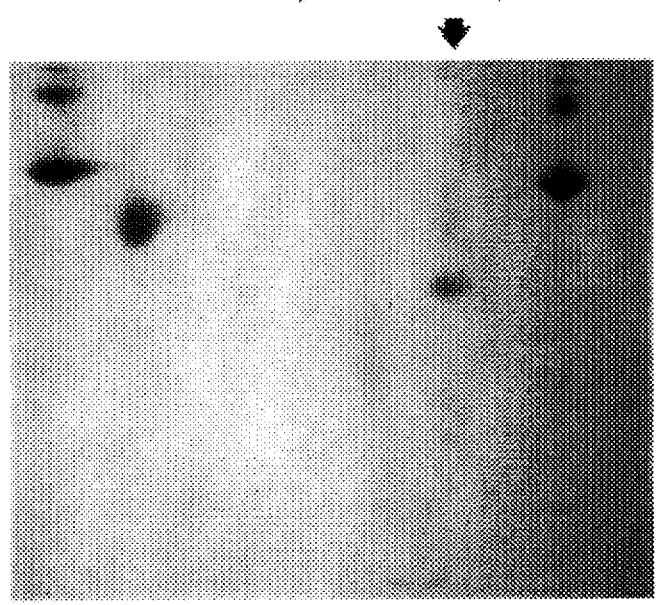
Native-PAGE

DEACETOXYCEPHALOSPORIN C HYDROXYLASE

This application is a continuation of application Ser. No. 07/412,761, filed Sep. 26, 1989, which is now abandoned.

BACKGROUND OF THE INVENTION

The biosynthetic pathway in the elaboration of cephalosporin C involves the action of several enzymes. Briefly, ACV synthetase elaborates the tripeptide, L-α-aminoadipyl-L-cysteinyl-D-valine, and the tripeptide (ACV) is converted by isopenicillin N synthetase (IPNS) to isopenicillin N. The latter is isomerized to penicillin N via epimerase enzyme (IPN epimerase or IPNE) and deacetoxycephalosporin C DAOC synthetase ("expandase") converts penicillin N to deacetoxycephalosporin C. The enzyme hydroxylase, deacetylcephalosporin C synthetase (DOAC hydroxylase), converts DAOC to deacetylcephalosporin C (DAC) and cephalosporin C is produced via the action of the acetyl transferase, cephalosporin C synthetase, on DAC.

The biosynthetic pathway of cephalosporin C has been the subject of extensive study. Jensen, S. E., et al., 1985, *J. Antibiot.*, 38, 263–265, reported two separate enzymes, expandase and hydroxylase, in *Streptomyces clavuligerus*. Cortes, J., et al., 1987, *Gen. Microbiol.*, 133, 3165–3174, reported on the purification and characterization of deacetoxycephalosporin C synthetase from *Streptomyces lactamdurans*. Dotzlaf, J. E., Yeh, W-K., 1987, *J. Bacteriol.*, 169, 1611–1618, described a bifunctional expandase/hydroxylase from *Cephalosporium acremonium* (U.S. Pat. No. 4,753,881). Rollins, M. J., et al., 1988, *Can. J. Microbiol.*, 34, 1196–1202, reported the partial purification of DOAC synthase isolated from *Streptomyces clavuligerus*. Recently, Yeh and Dotzlaf reported the purification of expandase from *Streptomyces clavuligerus* as well as recombinant *Escherichia coli*.

The availability of the enzymes involved in the cephalosporin C biosynthetic pathway would be of great value. The enzymes, particularly in a purified form, are of use in reverse genetic approaches to the genes of the cephalosporin C-producing microorganisms. Cloning of such genes in other organisms can provide higher yields of cephalosporin C. In addition, the isolated enzymes can be used to study the cell-free conversion of various substrates to produce structurally modified β-lactam antibiotics, for example, as was done by Baldwin, U.S. Pat. No. 4,666,835, in producing substituted penicillins. Accordingly, the isolation and purification of these enzymes of the pathway is of ongoing importance in the search for more effective antimicrobial agents and in the production of cephalosporin C via recombinant technology.

This invention relates to the enzyme, deacetylcephalosporin C synthetase (DACS), also referred to as deacetoxycephalosporin C hydroxylase. In particular, it relates to DACS obtained from *Streptomyces clavuligerus* and a method for obtaining the enzyme in purified form.

BRIEF DESCRIPTION OF THE DRAWINGS

FIG. 4A is a copy of the SDS-PAGE gel picture for hydroxylase.

FIG. 4B is a copy of the NATIVE-PAGE gel picture for hydroxylase.

DETAILED DESCRIPTION

Figure 1:
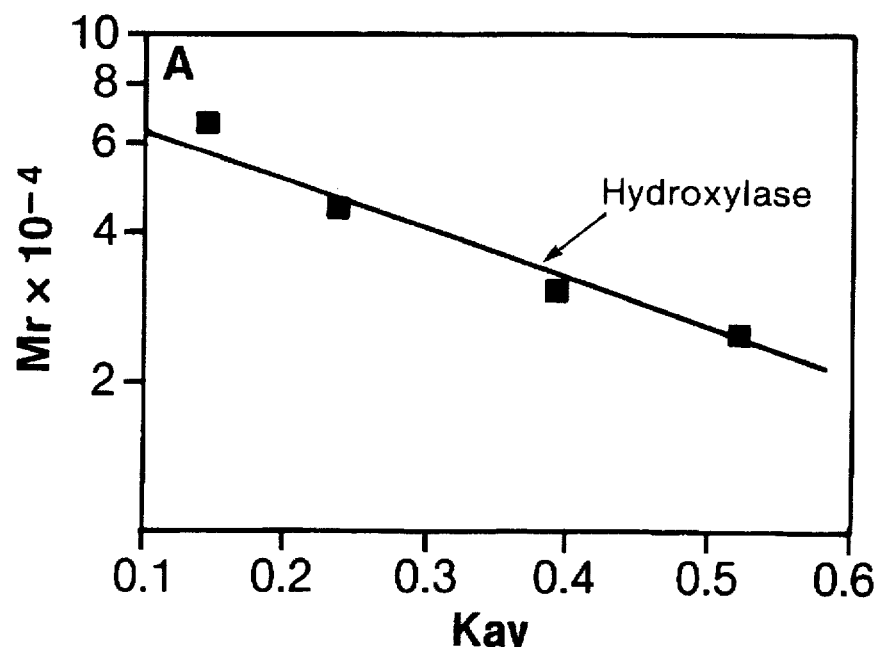
FIG. 1A is a plot of the molecular weight of hydroxylase as determined by gel filtration.
FIG. 1B is a plot of the molecular weight of hydroxylase as determined by SDS-PAGE.
Figure 1:
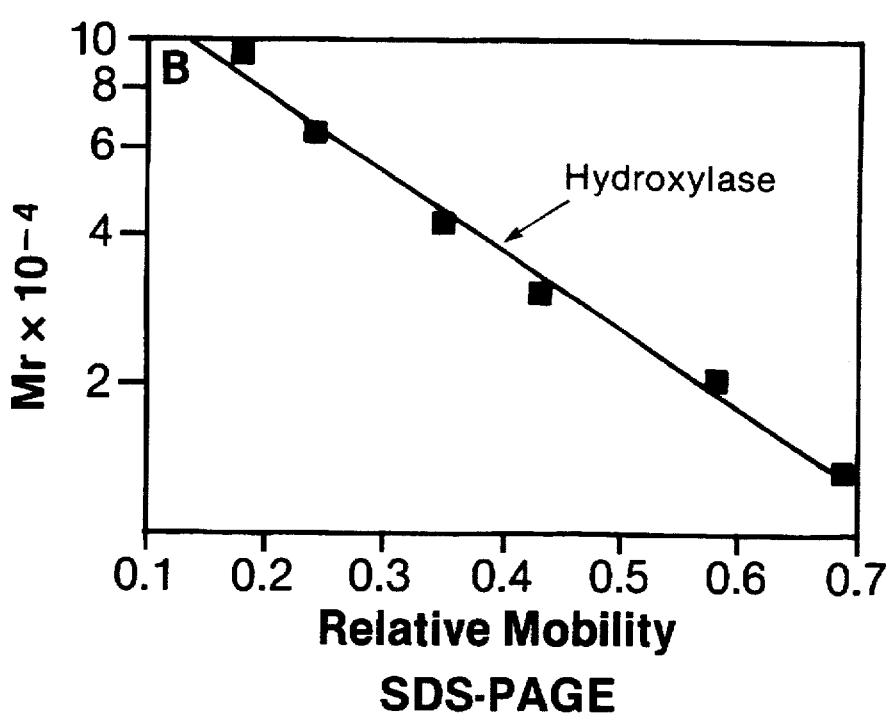

The deacetoxycecphalosporin C hydroxylase (DAOC hydroxylase) of the invention can be obtained from cell extracts of strains of *Streptomyces clavuligerus* and is provided in greater than 90% purity. The highly purified native enzyme (92% purity) has a molecular weight of 35,000 dalton as estimated by gel filtration using Ultragel AcA54 gel (FIG. 1A). The minimum molecular weight is 38,000 dalton as determined by SDS-PAGE (FIG. 1B). The hydroxylase is a monomeric enzyme.

The amino acid composition of DAOC hydroxylase is shown below in TABLE 1. The amino acid composition was determined by the method described by Dotzlaf and Yeh (1987) *J. Bacteriol.*, 169, 1611–1618.

TABLE 1

| Amino acid composition of DAOC hydroxylase from *S. clavuligerus* ||
|---|---|
| Amino Acid | No. of residues per 35,000-dalton |
| Asp + Asn | 25 |
| Thr | 26[a] |
| Ser | 27[a] |
| Glu + Gln | 32 |
| Pro | 18 |
| Gly | 31 |
| Ala | 37 |
| Cys | 5[b] |
| Val | 21 |
| Met | 9 |
| Ile | 8 |
| Leu | 23 |
| Tyr | 11 |
| Phe | 17 |
| His | 8 |
| Lys | 6 |
| Arg | 19 |
| Trp | 2[c] |

[a]Determined by extrapolation to zero time of hydrolysis.
[b]Determined as cysteic acid.
[c]Determined by hydrolysis in the presence of thioglycolic acid.

The 28-residue amino-terminal sequence of the native hydroxylase protein has been determined and is as follows: Ala-Asp-Thr-Pro-Val-Pro-Ile-Phe-Asn-Leu-Ala-Ala-Leu-Arg-Glu-Gly-Ala-Asp-Gln-Glu-Lys-Phe-Phe-Glu-His-Val-His-Leu.

A 9-residue amino-terminal sequence (internal sequence) was obtained by degradation of the native hydroxylase protein during its purification. Its sequence is as follows: Thr-Gly-Ser-Tyr-Thr-Asp-Tyr-Ser-Thr.

The 3-residue carboxy-terminal sequence of the native protein was determined as follows: Pro-Arg-Ala.

The DAOC hydroxylase requires external α-ketoglutarate, ferrous ion and oxygen for catalytic activity. Ferrous ion is required for expression of maximum enzymatic activity, which drops to 2% of maximum without external $Fe^{2+}$. Ferrous ion was not replaceable by any of the following ions: $Mg^{2+}$, $Mn^{2+}$, $Co^{2+}$, $Ca^{2+}$, $Cu^{2+}$, $Ni^{2+}$, $Zn^{2+}$, sodium or potassium. External ferric ion can replace ferrous ion with retention of maximum activity when in the presence of a suitable reducing agent such as dithiothreitol (DTT) or ascorbate. Reduced glutathione in the presence of ascorbate is as effective in stimulating enzyme activity. β-Mercaptoethanol displays little stimulating effect. The maximum catalytic activity observed with external ferrous ion in the presence of DTT or ascorbate drops some 80% when DTT and ascorbate are not present.

The catalytic activity observed for the enzyme with the required $Fe^{2+}$, α-ketoglutarate and $O_2$ is stimulated by DTT or ascorbate but not by ATP. In the absence of any reducing agent such as DTT, the hydroxylase activity is reduced by about 5-fold.

The enzyme reaction, DAOC to DAC, is optimal at pH 7.0–7.4 in 15 mM 3-(N-morpholino)propanesulfonic acid buffer (MOPS buffer) and at a temperature of about 29° C. The MOPS buffer is a preferred buffer for use with the enzyme, since at an optimal pH substitution of MOPS buffer by HEPES buffer and Tris-HCl buffer caused, respectively, a 7% and 27% reduction in enzyme activity.

The effect of metal chelators and sulfhydryl reagents on DAOC hydroxylase has been determined and the results shown below in TABLE 2.

TABLE 2

Effect of Metal Chelators and Sulfhydryl Reagents on DAOC Hydroxylase

| Additive[1] | Concentration (mM) | Relative Activity (%) |
|---|---|---|
| None | — | 100 |
| o-Phenanthroline | 0.05 | 81 |
| | 0.5 | 0 |
| EDTA | 0.05 | 16 |
| | 0.5 | 0 |
| DTNB | 1 | 0 |
| NEM | 1 | 24 |
| Iodoacetic acid | 1 | 59 |

[1]EDTA — ethylenediamine tetraacetic acid
DTNB — 5,5'-dithiobis-2-nitrobenzoic acid
NEM — N-ethylmaleimide The stimulation in catalytic activity by DTT, as noted above, coupled with the susceptibility to inhibition by sulfhydryl reagents (TABLE 2) indicates that at least one sulfhydryl group of the enzyme is essential for activity. The number and location of the putatively important sulfhydryl residue(s) has thus far not been determined.

In addition to the primary catalytic activity of DAOC hydroxylase, i.e., the conversion of deacetoxycephalosporin C to deacetylcephalosporin C (DAC), the enzyme was effective in mediating the hydroxylation of 3-exomethylenecephalosporin C [7β-(α-aminoadipoylamino)-3-exomethylenecepham-4-carboxylic acid, EMCC] to DAC. The hydroxylase provided by this invention unexpectedly demonstrated weak catalytic activity in the ring-expansion of penicillin N to DAOC, the latter being converted to DAC. It appears that this ring expansion activity is an intrinsic property of the DAOC hydroxylase rather than being attributable to the expandase enzyme also produced by S. clavuligerus.

The relative $V_{max}$ values for the three activities of the DAOC hydroxylase are shown below in TABLE 3.

TABLE 3

Percent Catalytic Activities for DAOC Hydroxylase

| Reaction | $V_{max}$ |
|---|---|
| Penicillin N to DAOC | 1.4 |
| DAOC to DAC | 100 |
| EMCC to DAC | 37 |

Several compounds were evaluated as substrates for the purified enzyme to determine its substrate specificity. The compounds evaluated and the results are shown below in TABLE 4. The results were obtained by HPLC analysis.

TABLE 4

Substrate Specificity of DAOC Hydroxylase

| Compound | Sp. Activity (mU/mg) | Relative Activity (%) |
|---|---|---|
| DAOC | 159.2 | 100 |
| EMCC[1] | 58.1 | 36.5 |
| Carba-DAOC[2] | 3.0 | 1.9 |
| Iso-DAOC[3] | 1.3 | 0.8 |

[1]7β-(D-α-aminoadipamido)-3-exomethylenecepham-4-carboxylic acid
[2]1-carba(1-dethia)deacetoxycephalosporin C
[3]7β-(L-α-aminoadipamido)-3-methyl-3-cephem-4-carboxylic acid, "isodeacetoxycephalosporin C"

As shown in the table, the enzyme was fairly efficient in the conversion of EMCC to DAC, 36.5% relative to the DAOC to DAC conversion. The 1-carba-DAOC and iso-DAOC did not serve as effective substrates for hydroxylase under the conditions described hereinabove for optimal catalysis of the hydroxylase.

The important kinetic parameters for the enzyme have been determined under the optimal reaction conditions noted hereinabove. The $K_m$ of the hydroxylase for DAOC or for α-ketoglutarate were obtained at a saturated concentration of either substrate (300 μM DAOC or α-KG). The respective $K_m$s as determined by the Lineweaver-Burk method were 50 μM (DAOC) and 10 μM (α-KG).

The $K_a$ of the hydroxylase for ferrous ion was similarly determined as 20 μM.

The $V_{max}$ of the hydroxylase was determined as 0.45 μM of DAC formed per minute per milligram of protein.

Figure 2:
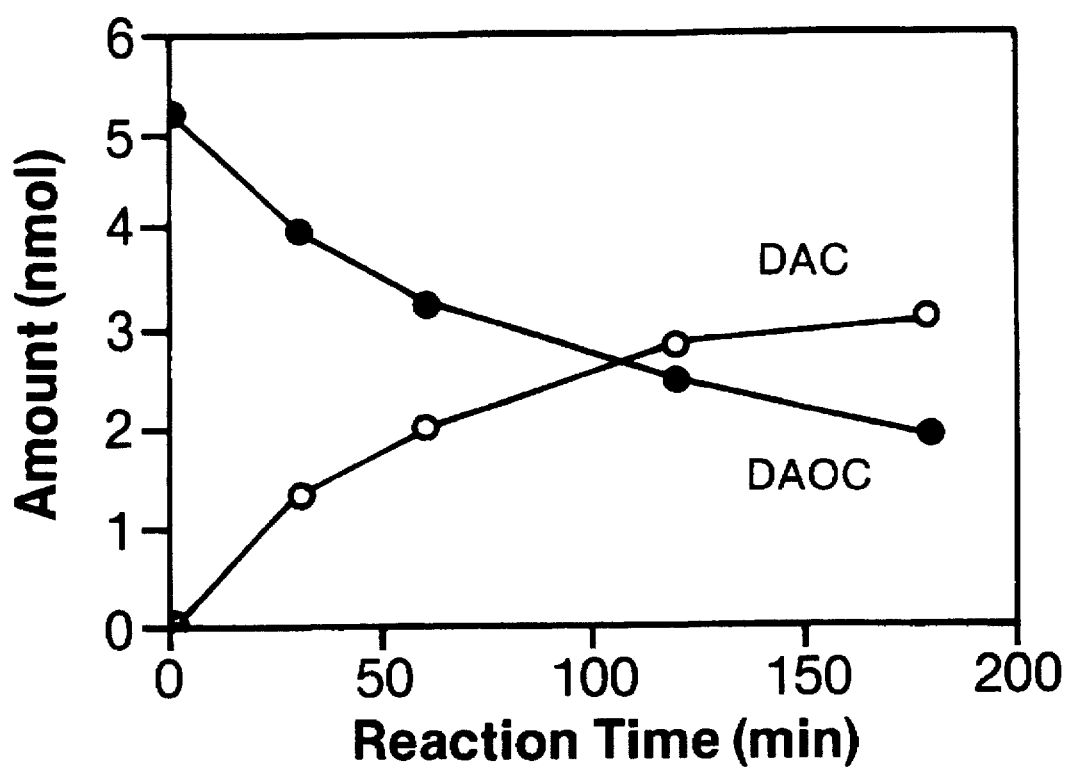
FIG. 2 is a plot of the DAOC to DAC Reaction Stoichiometry.

The stoichiometry of the hydroxylase conversion of DAOC to DAC was determined. The molar ratio for DAC-formation/DAOC-disappearance during a 3 h reaction remained in the range of 0.91–1.00 as shown by the plot in FIG. 2. The conversion of DAOC to DAC was only partially complete (58%) under the reaction conditions.

This invention also provides a process for isolating the DAOC hydroxylase from crude cell-free extracts of the enzyme.

The DAOC hydroxylase can be obtained from extracts of cephalosporin C and cephamycin C-producing strains of Streptomyces clavuligerus. It can also be obtained from cells of Streptomyces lipmanii and Streptomyces lactamdurans. In contrast to Cephalosporium acremonium which produces a bifunctional enzyme expandase/hydroxylase as described by U.S. Pat. No. 4,753,881, S. clavuligerus produces an expandase enzyme and a hydroxylase as separate enzymes. A number of S. clavuligerus strains are available for use in the process of this invention. One such strain is ATCC No. 27064 deposited in the American Type Culture Collection. A preferred strain is NRRL 18491 deposited in the culture collection of the Northern Regional Research Laboratories of the Department of Agriculture, Peoria, Ill.

The DAOC hydroxylase is recognized as unstable and, accordingly, was difficult to isolate and obtain in a high state of purity from cell-free extracts. For example, DAOC hydroxylase from crude extracts of the organism when prepared at 4° C. in 15 mM Tris-HCl buffer, pH 7.5, exhibited a half-life of only 12 h. Addition of phenylmethylsulfonyl fluoride (PMSF) and ethyl alcohol during the preparation of the extracts, which are known to partially protect DAOC synthetase from inactivation, had no effect on the stability of the hydroxylase.

The process of this invention comprises the use of a hydroxylase stabilizing buffer which is used both in the preparation of crude cell-free extracts of the enzyme and during the isolation and purification thereof. The stabilizing buffer, referred to herein as buffer A, comprises 15 mM MOPS buffer, pH 7.3, containing 1 mM uric acid, 1 mM mannitol and 0.1M KCl. When the crude cell-free extracts are prepared in stabilizing buffer, the half-life of the hydroxylase improved 6-fold over that observed with the Tris-HCl buffer, i.e., to 72 hours. With this improved buffer system, the ability to carry out the multiple chromatographic steps required to isolate the enzyme in a high state of purity was greatly enhanced.

The process of this invention comprises, in addition to the use of the stabilizing buffer, controlled cell disruption by sonic treatment in the preparation of the cell-free extracts, and a combination of chromatographic steps. The process provides hydroxylase purified to near electrophoretic homogeneity with a specific activity of about 0.45 U/mg protein as extrapolated from the first Mono Q FPLC as described hereinafter.

The preparation of the cell-free extract and the several chromatographic steps were carried out at a temperature between about 0° C. and about 4° C. Buffer A is degassed prior to use.

According to the process of this invention, fresh cells of S. clavuligerus are suspended in 15 mM MOPS, pH 7.3, in the presence of 1 mM uric acid, 1 mM mannitol and 0.1M KCl. This buffer system is referred to hereinafter as "buffer A". The cells are broken up at a temperature of about 0° C. to 4° C. by controlled sonication of the cell suspension. "Controlled sonication" as used herein refers to intermittent sonication of a suspension of S. clavuligerus cells in buffer A maintained at a temperature of 0° C. to about 4° C. The sonicator is run in intervals which may vary from about 2 to 6 intervals of about 15-25 seconds in duration. After each sonication interval the sonicator is turned off and the suspension is allowed to rest for about 30 seconds to about two minutes before the next sonication interval to maintain the temperature at or below 4° C. Preferably, about 3 to 5 intervals of about 20 seconds each are used in preparing the extract. The description of hydroxylase containing cells of S. clavuligerus by controlled sonication results in cell-free extracts having higher enzymatic activity. Constant sonication or sonication over an extended period of time results in inactivation of the hydroxylase. Complete sonication will result in the freeing of more protein from the cells but an extract with less specific activity. The sonication is preferably carried out in four intervals of 20 seconds each with a short rest period of about 30 seconds to one minute between intervals. The sonicate is centrifuged at 47,000×g for 30 minutes to provide the crude cell-free extract of the hydroxylase.

Figure 3:
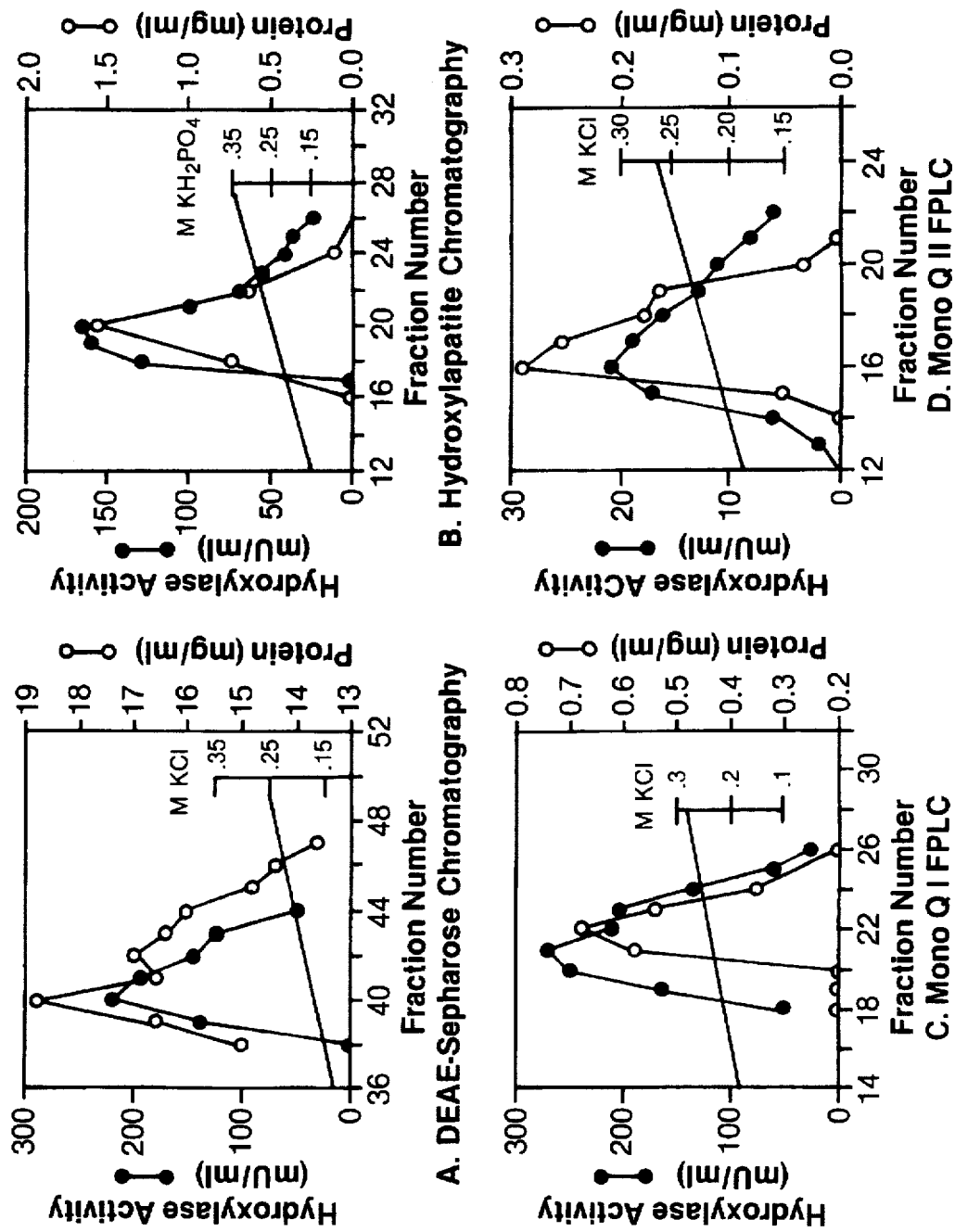
FIG. 3A is a plot of the hydroxylase DEAE-Sepharose chromatogram.
FIG. 3B is a plot of the hydroxylase hydroxylapatite chromatogram.
FIGS. 3C and 3D are plots of the hydroxylase Mono Q I and II FPLC chromatograms, respectively.

The crude cell-free extract prepared as described above is chromatographed over a weak anion exchange resin of the derivatized cellulose type such as a diethylaminoethyl cellulose, preferably DEAE-Sepharose (Pharmacia, Inc., Piscataway, N.J.). The resin is equilibrated with buffer A prior to use and is washed with buffer A, preferably in an amount corresponding to about one bed volume prior to elution. The bound proteins are eluted with a linear gradient of KCl (0.1M–0.5M) in buffer A. The DAOC hydroxylase is eluted mainly as a single activity peak separated from DAOC synthase. A plot of a typical elution pattern is shown in FIG. 3A.

The fractions containing about 40% of the total hydroxylase activity are combined, concentrated to a smaller volume and the concentrate fractionated with ammonium sulfate. The fraction obtained at 45%–70% $NH_4SO_4$ concentration is chromatographed over a suitable gel such as Bio-Gel A0.5 m or Bio-Gel P-60 (Bio-Rad Laboratories, Richmond, Calif.) or, preferably Ultragel AcA54 (IBF Biotechnics, Villeneuve-la-Garenne, France). The gel is equilibrated with buffer A prior to use and protein is eluted with buffer A. The hydroxylase activity elutes as a single activity peak. The fractions containing about 60% of the total hydroxylase activity are pooled and chromatographed over hydroxylapatite previously equilibrated with buffer A. The hydroxylapatite is first washed with buffer A in an amount corresponding to about two bed volumes. The bound proteins are eluted with a linear gradient of potassium phosphate (0–100 mM) in buffer A. The hydroxylase activity is eluted as a single activity peak as shown by the plot of a typical run shown in FIG. 3B.

Fractions of the eluant which contain about 70% of the total hydroxylase activity are combined and subjected to fast protein liquid chromatography (FPLC) over a strongly anionic exchange resin such as Mono Q (Pharmacia, Inc., Piscataway, N.J.). The resin is equilibrated with buffer A prior to use and bound proteins are eluted with a linear salt gradient of KCl (0.1M–0.5M) in buffer A. As shown in FIG. 3C, a plot of a typical run, the hydroxylase is eluted as a single activity peak.

Fractions containing the highest hydroxylase activity are combined and concentrated and the concentrate chromatographed over a suitable gel such as Bio-Gel P-60 (Bio-Rad Laboratories, Richmond, Calif.) or Superose A12 (Pharmacia, Inc., Piscataway, N.J.). The gel is equilibrated before use with buffer A and the hydroxylase eluted as a single activity peak with buffer A.

The fractions containing the highest activity for the enzyme were combined and again chromatographed over the strong anionic resin such as Mono Q which is prior equilibrated with buffer A. Fractions containing the hydroxylase activity are combined. Results of the second Mono Q chromatography of a typical purification run are shown in FIG. 3D of the drawings.

The purity of the DAOC hydroxylase obtained after the second FPLC of the process is shown by analysis of the eluant by SDS-PAGE. As shown in FIG. 4A of the drawings, the FPLC eluent migrated as major and minor protein bands. From a laser densitometric scan of the gel, the major protein was about 92% pure. An amino-terminal sequence analysis of the remaining 8% minor protein shown indicates that the minor protein is a degradation product of the major hydroxylase protein. Only a broad single band is observed from protein analysis by NATIVE-PAGE (FIG. 4B).

Hydroxylase of the highest purity is obtained as described above in the seventh step, i.e., the second FPLC. Because of some apparent inactivation of the protein over the gel chromatography of step 6 and the second FPLC step 7, there is a loss of enzymatic activity from that obtained from the first FPLC in step 5. The hydroxylase obtained after the first FPLC of step 5 is about 70% pure, while that obtained after the second FPLC is above 90% pure. The activity obtained after step 5 is generally about 1,200 mU, while after step 7 (second FPLC) the activity is usually about 90 mU. In terms of specific activity after step 5, the specific activity is usually about 300 mU/mg, while after step 7 it is about 125–130 mU/mg.

The hydroxylase obtained after completion of step five, owing to its high activity and substantial purity, can be suitable for uses where the highest purity is not required. For example, the hydroxylase can be used in cell-free conversions of DAOC to DAC or for conversion of EMCC to DAC by the process provided herein.

Accordingly, the hydroxylase provided herein is in substantially pure form, which as used herein refers to a purity of from about 70% to greater than 90%.

The activity of the DAOC hydroxylase is determined throughout the process by the following assay method. The hydroxylase activity was determined by monitoring DAC formation from DAOC at 260 nm with HPLC as described by Dotzlaf, J. E., and Yeh, W.-K. (1987) *J. Bacteriol.*, 169, 1611–1618. A typical assay mixture is of 1 ml volume and contains 0.3 µmol of DAOC, 0.3 µmol of α-ketoglutarate, 0.1 µmol of ferrous sulfate, 0.25 µmol of ascorbate, 1 µmol of DTT, 0.05 µmol of ATP, and between about 0.00005 to 0.003 units of the enzyme in 15 mM MOPS buffer, pH 7.3. The enzymatic reaction is initiated by adding the DAOC and the reaction is conducted for 20 minutes at 29° C. DAC formation is linear with reaction time for up to 40 minutes. One unit of enzyme activity is defined as the amount of hydroxylase required to cause formation of one µmol of DAC per minute from DAOC under the above-described assay conditions.

The specific activity of the hydroxylase is defined as units per milligram of protein.

The standard proteins used in the determination of molecular weight by SDS-PAGE as shown in FIG. 4A and the plot thereof in FIG. 1B were phosphorylase B (MW 92,000), bovine serum albumin (MW 66,200), ovalbumin (MW 45,000), carbonic anhydrase (MW 31,000), soybean trypsin inhibitor, and ribonuclease (MW 13,700).

The protein content is determined by the method of Bradford using bovine serum albumin as the standard (Bradford, M. M., 1979, *Anal. Biochem.*, 72, 248–254).

This invention further provides a process for preparing deacetylcephalosporin C which comprises contacting in the presence of oxygen, ferrous ion, and α-ketoglutarate in an aqueous medium at a pH between about 7.0 and about 7.5 7β-(D-α-aminoadipamido)-3-exomethylenecepham-4-carboxylic acid with deacetoxycephalosporin C hydroxylase.

The process is carried out at a temperature between about 25° C. and about 35° C. and, preferably, in the range of about 27° C. to about 30° C. A preferred pH is about pH 7.3. The most preferred conditions for carrying out the process are those under which the hydroxylase exhibits its optimum activity as described hereinabove.

The process is preferably carried out in the presence of a reducing agent which generally results in enhanced yields.

The term "reducing agent" as used herein refers to the reagents commonly used in enzyme technology to maintain an enzyme or a co-factor thereof in a reduced state and includes, for example, ascorbate, dithiothreitol (DTT), dithioerythritol, and the like. Combinations of reducing agents is also meant to be included in the term. For example, DTT and ascorbate can be used in combination as well as the combination ascorbate and reduced glutathione.

The concentration of ferrous ion used in the process may vary; however, a concentration between about 0.05 mM and 0.2 mM is suitable. Higher concentrations may be employed. α-Ketoglutarate is used at a concentration between about 0.05 mM and about 0.6 mM and, preferably, at a concentration of about 0.3 mM.

The process is preferably carried out in an open vessel which affords an adequate oxygen supply. However, with large-scale reactors, oxygen can be bubbled into the reactor to insure an adequate supply for the enzyme.

The process can be carried out in an aqueous cell-free system or, alternatively, with an immobilized enzyme in a column reactor. In the latter method the aqueous medium containing the starting material, ferrous ion, α-KG and reducing agent can be poured through the column to effect the reaction.

The following Example is provided to further illustrate the invention and is not intended to be limiting thereof.

EXAMPLE 1

Isolation and Purification of Deacetoxycephalosporin C Hydroxylase

*Streptomyces clavuligerus* NRRL 18491 was grown in a 150-liter fermenter by employing the conditions described by Nagarajan, R., et al., (1971) *J. Amer. Chem. Soc.*, 93, 2308–2310. After 16 h, cells were harvested by centrifugation, washed with 15 mM MOPS, pH 7.3, in the presence of 1 mM uric acid, 1 mM mannitol and 1.0M KCl and then with a 0.1M KCl buffer, and were stored at −70° C. until used.

Fresh cells (1 kg, net weight) were divided into four 250 g portions and each portion was resuspended in 15 mM MOPS, pH 7.3, in the presence of 1 mM uric acid, 1 mM mannitol and 0.1M KCl (buffer A) to a total volume of 250 ml. Each of the four suspensions were sonicated at 4° C. for 4 separate periods of sonication of 20 seconds each with a rest period between sonic treatments. The sonicate was centrifuged at 47,000×g for 30 minutes and the supernatant was separated as the crude cell-free extract of hydroxylase. The total crude extract analyzed for 2,833 mg of protein, had an activity (mU) of 20,433 and a specific activity (mU/mg) of 7.2.

As each of the four crude extracts were obtained, it was applied to a DEAE-Sepharose (Pharmacia, Inc., Piscataway, N.J.) column measuring 2.6 cm×75 cm which was previously equilibrated with buffer A. After all four extracts were added, the column was washed with one bed volume of buffer A and bound proteins were eluted with a linear gradient of KCl (0.1–0.5M) in buffer A. DAOC hydroxylase was eluted mainly as a single activity peak as shown in FIG. 3A and well separated from DAOC synthase (not shown in FIG. 3A). In addition to the major separable synthase activity, a minor synthase activity appeared to coelute with the hydroxylase activity.

The five fractions (#39–43) containing about 40% of the total hydroxylase activity were pooled, concentrated and fractionated by ammonium sulfate. A portion (2.5 ml) of the fraction at 45%–70% saturation of ammonium sulfate was loaded onto an Ultragel AcA54 (IBF Biotechnics, Villeneuve-la-Garenne, France) column (1.6×95 cm) previously equilibrated with buffer A. The protein was eluted with buffer A. Hydroxylase was eluted as a single activity peak and fractions 39–43 containing 60% of the total hydroxylase activity were pooled and applied to a hydroxylapatite column (1.0 cm×60 cm) which was previously equilibrated with buffer A. The column was washed with two-bed volumes of buffer A and bound proteins were eluted with a linear gradient of potassium phosphate (0–100 mM) in buffer A. The hydroxylase was eluted as a single activity peak as shown by FIG. 3B.

The three fractions (#18–20) containing 70% of the total hydroxylase activity were pooled and applied to a Mono Q (Pharmacia, Inc., Piscataway, N.J.) column (0.5 cm×5 cm) previously equilibrated with buffer A. Bound protein was eluted with a linear gradient of KCl (0.1–0.5M) in buffer A. Hydroxylase was eluted as a single activity peak as shown by FIG. 3C.

Fractions 21–23 with the highest hydroxylase activity were pooled, concentrated to 0.2 ml with a Centricon-30 (Amicon) and the concentrate applied to a Superose A12 (Pharmacia Inc., Piscataway, N.J.) column (1.6 cm×85 cm) previously equilibrated with buffer A. A single activity peak for hydroxylase was observed and fractions 47 and 48 having the highest hydroxylase activity were pooled and applied to a second Mono Q column (0.5 cm×5 cm) previously equilibrated with buffer A. The Mono Q column was eluted as before and fractions 15–20 containing the hydroxylase activity were stored at −70° C. for further use.

The course of the hydroxylase purification over the chromatographic steps described above is shown in the following TABLE 5.

TABLE 5

Purification of DAOC Hydroxylase From *S. clavuligerus*

| Step | Protein (mg) | Activity (mU) | Sp. Act. (mU/mg) | Recovery (%) |
|---|---|---|---|---|
| Crude Extract | 2,833 | 20,433 | 7.2 | 100 |
| DEAE-Sepharose Eluate | 854 | 8,184 | 9.6 | 40 |
| 45–70% (NH$_4$)$_2$SO$_4$ Fraction | 176 | 2,607 | 14.8 | 13 |
| Ultrogel AcA54 Eluate | 47.3 | 2,687 | 56.8 | 13 |
| Hydroxylapatite Eluate | 16.7 | 1,648 | 98.7 | 8 |
| Mono Q I Eluate | 3.94 | 1,200 | 304.6 | 6 |
| Superose 12 Eluate | 1.96 | 471 | 241.0 | 2 |
| Mono Q II Eluate | 0.69 | 88 | 127.5 | 0.4 |

As shown in the table, there was partial enzyme inactivation across the last two steps, i.e., Superose A12 FPLC and the Mono Q II FPLC. Despite the partial inactivation, highly pure hydroxylase was obtained. Based on the main protein from the Mono Q II eluate by SDS-PAGE, the hydroxylase obtained was about 92% pure.

We claim:

1. Deacetoxycephalosporin C hydroxylase in substantially pure form which has a molecular weight of about 35,000 dalton as determined by gel filtration and about 38,000 dalton as determined by SDS-PAGE;

which is a monomeric molecule;

which has an amino acid composition as follows:

| Amino Acid | Number of Residues per 35,000-dalton |
|---|---|
| Asp + Asn | 25 |
| Thr | 26 |
| Ser | 27 |
| Glu + Gln | 32 |
| Pro | 18 |
| Gly | 31 |
| Ala | 37 |
| Cys | 5 |
| Val | 21 |
| Met | 9 |
| Ile | 8 |
| Leu | 23 |
| Tyr | 11 |
| Phe | 17 |
| His | 8 |
| Lys | 6 |
| Arg | 19 |
| Trp | 2; | which has the following 28-residue amino-terminal sequence: Ala-Asp-Thr-Pro-Val-Pro-Ile-Phe-Asn-Leu-Ala-Ala-Leu-Arg-Glu-Gly-Ala-Asp-Gln-Glu-Lys-Phe-Phe-Glu-His-Val-His-Leu;

which has an internal sequence having a 9-residue amino-terminal sequence as follows: Thr-Gly-Ser-Tyr-Thr-Asp-Tyr-Ser-Thr;

which has a 3-residue carboxy-terminal sequence as follows: Pro-Arg-Ala;

which requires ferrous ion, α-ketoglutarate and oxygen for expression of catalytic activity;

which has enhanced catalytic activity in the presence of dithiothreitol and ascorbate;

which exhibits the following kinetic parameters:
$K_m$ (DAOC)=50 µM
$K_m$ (α-ketoglutarate)=10 µM
$K_a$ (Fe$^{++}$)=20 µM; and which converts 7β-(α-aminoadipamido)-3-exomethylenecepham-4-carboxylic acid to deacetylcephalosporin C.

2. A process for preparing the deacetoxycephalosporin C hydroxylase of claim 1 which comprises the steps, A) chromatographing a crude cell-free extract of deacetoxycephalosporin C hydroxylase, obtained by controlled sonic disruption of deacetoxycephalosporin C hydroxylase containing cells, over a weak anion exchange resin and eluting bound proteins with a linear KCl gradient of 0.1M–0.5M, followed by concentrating the deacetoxycephalosporin C hydroxylase-rich portion of the eluate containing about 40% of the total hydroxylase activity;

B) fractionating the concentrated elutate of step A with ammonium sulfate and concentrating the fraction obtained at an ammonium sulfate concentration of about 45% to about 70%;

C) chromatographing the concentrate of step B over a size exclusion gel and combining the hydroxylase eluate fractions containing about 60% of the total hydroxylase activity;

D) chromatographing the combined fractions of step C over hydroxylapatite, eluting bound protein with a linear potassium phosphate gradient of 0–100 mM, and combining eluate fractions containing about 70% of the total hydroxylase activity; and E) chromatographing over a strong anionic resin via Fast Protein Liquid Chromatography the combined eluate of step D, eluting bound protein with a linear KCl gradient of 0.1M–0.5M, to provide the hydroxylase of claim 1 in a purity of about 70%; wherein steps A through E are carried out at a temperature between about 0° C. and about 4° C.; and wherein each of steps A through E are carried out in buffer A comprising 15 mM 3-(N-morpholino)propanesulfonic acid buffer, pH 7.0–7.4, containing 1 mM uric acid, 1 mM mannitol, and 0.1M KCl.

3. The process of claim 2 which comprises the further steps of F) chromatographing in buffer A the eluate fractions of step E containing the highest hydroxylase activity over a size exclusion gel, eluting the hydroxylase with buffer A, and combining the eluate fractions containing the highest hydroxylase activity; and G) rechromatographing in buffer A the combined fractions over a strong anionic exchange resin, eluting the bound protein with a linear KCl gradient of 0.1M–0.5M in buffer A, and combining the eluate fractions containing hydroxylase activity to provide the hydroxylase of claim 1 in a purity of greater than 90%.

4. The process of claim 2 wherein, in step A, the crude cell-free extract is obtained from *Streptomyces clavuligerus* cells.

5. The process of claim 2 wherein, in step A, the weak anion exchange resin is DEAE-Sepharose.

6. The process of claim 2 where the strong anion resin of step E is Mono Q.

* * * * *